US009920203B2

(12) United States Patent
Abe et al.

(10) Patent No.: US 9,920,203 B2
(45) Date of Patent: Mar. 20, 2018

(54) PEARLESCENT PIGMENT, PROCESS FOR PRODUCING THE SAME, COATING COMPOSITION AND MULTILAYERED COAT

(75) Inventors: Takashi Abe, Chuo-ku (JP); Satoru Matsuzaki, Chuo-ku (JP); Shotoku Takami, Chuo-ku (JP)

(73) Assignee: DAINICHISEIKA COLOR & CHEMICALS MFG. CO., LTD., Tokyo (JP)

(*) Notice: Subject to any disclaimer, the term of this patent is extended or adjusted under 35 U.S.C. 154(b) by 0 days.

(21) Appl. No.: 13/533,485

(22) Filed: Jun. 26, 2012

(65) Prior Publication Data
US 2012/0269986 A1 Oct. 25, 2012

Related U.S. Application Data

(62) Division of application No. 11/992,977, filed as application No. PCT/JP2006/319713 on Oct. 2, 2006, now abandoned.

(30) Foreign Application Priority Data

Oct. 3, 2005 (JP) ................. 2005-290148

(51) Int. Cl.
*C09C 1/00* (2006.01)
*A61K 8/26* (2006.01)
*A61Q 1/02* (2006.01)
*B82Y 30/00* (2011.01)
*C09D 5/29* (2006.01)
*C09D 5/36* (2006.01)
*C09D 11/037* (2014.01)
*C09D 11/322* (2014.01)
*A61K 8/02* (2006.01)

(52) U.S. Cl.
CPC .......... *C09C 1/0015* (2013.01); *A61K 8/0262* (2013.01); *A61K 8/26* (2013.01); *A61Q 1/02* (2013.01); *B82Y 30/00* (2013.01); *C09C 1/0021* (2013.01); *C09D 5/29* (2013.01); *C09D 5/36* (2013.01); *C09D 11/037* (2013.01); *C09D 11/322* (2013.01); *A61K 2800/434* (2013.01); *A61K 2800/436* (2013.01); *A61K 2800/621* (2013.01); *A61K 2800/651* (2013.01); *C01P 2004/54* (2013.01); *C01P 2004/62* (2013.01); *C01P 2004/64* (2013.01); *C09C 2200/1004* (2013.01); *C09C 2200/505* (2013.01)

(58) Field of Classification Search
CPC .......... A51K 2800/43; A51K 2800/434; A51K 2800/436; A61K 8/02; A61K 8/11; A61K 8/26; B82Y 30/00; C01P 2004/54; C01P 2004/62; C01P 2004/64; C09C 1/0015; C09C 1/0021; C09C 2200/1004; C09C 2200/505; C09D 11/037; C09D 11/322; C09D 5/29; C09D 5/36
USPC ...................... 427/535, 157, 560
See application file for complete search history.

(56) References Cited

U.S. PATENT DOCUMENTS

| | | | |
|---|---|---|---|
| RE21,693 E * | 1/1941 | Plechner ............ | C01G 23/0536 106/436 |
| 3,861,946 A * | 1/1975 | Waitkins ............... | C01F 11/466 106/415 |
| 4,494,993 A * | 1/1985 | Bernhard et al. ............ | 106/417 |
| 4,509,988 A | 4/1985 | Bernhard | |
| 4,615,940 A | 10/1986 | Panush et al. | |
| 4,676,838 A * | 6/1987 | Franz et al. .................. | 106/415 |
| 5,008,143 A | 4/1991 | Armanini | |
| 5,702,519 A | 12/1997 | Nitta et al. | |
| 6,096,378 A | 8/2000 | Komatsu et al. | |
| 6,517,628 B1 | 2/2003 | Pfaff et al. | |
| 6,579,355 B1 | 6/2003 | Schmidt et al. | |
| 6,717,628 B2 * | 4/2004 | Kumagawa et al. ........... | 349/38 |
| 6,777,085 B1 * | 8/2004 | Argoitia et al. .............. | 428/403 |
| 6,858,072 B1 * | 2/2005 | Li et al. ........................ | 106/415 |
| 7,067,157 B2 * | 6/2006 | Fukuda ..................... | A61K 8/26 423/625 |
| 2003/0047115 A1 * | 3/2003 | Bauer et al. .................. | 106/415 |
| 2004/0123779 A1 * | 7/2004 | Bagala, Sr. .......... | A61K 8/0254 106/415 |
| 2004/0166316 A1 * | 8/2004 | Noguchi ....................... | 428/402 |

FOREIGN PATENT DOCUMENTS

| | | |
|---|---|---|
| EP | 1 072 651 A1 | 1/2001 |
| JP | 9-255891 A | 9/1997 |
| JP | 2000-345096 A | 12/2000 |
| JP | 2001-11341 A | 1/2001 |
| JP | 2001-40241 A | 2/2001 |
| JP | 2001-146221 A | 5/2001 |

OTHER PUBLICATIONS

Teaney et al. "New effect pigments using innovative substrates".*
Teaney, S., et al., "New Effect Pigments Using Innovative Substrates," European Coatings Journal, Seite 90, Apr. 1999, pp. 1-6.
Japan Painting Contractors Association, Toryo Ganryo Binran, Revised 7th Edition, May 31, 1999, p. 384, Paragraph 4.5.3.
Maile, F.J., et al., "Effect Pigments—Past, Present and Future," Progress in Organic Coatings, vol. 54, 2005, pp. 150-163.
European Patent Office, Supplementary European Search Report for European Patent Application No. EP 06 81 1061, European Patent Office, Rijswijk, Netherlands, dated Nov. 7, 2011.

* cited by examiner

*Primary Examiner* — Dah-Wei D. Yuan
*Assistant Examiner* — Jose Hernandez-Diaz
(74) *Attorney, Agent, or Firm* — Hamre, Schumann, Mueller & Larson, P.C.

(57) ABSTRACT

This invention relates to a pearlescent pigment, which is composed of flaky alumina substrate particles produced by a hydrothermal process and coat layers formed on the flaky substrate particles and composed of at least one metal oxide including at least a titanium oxide. The metal oxide has an average particle size of from 1 to 500 nm. According to this invention, it is possible to provide a pearlescent pigment, which has wholly uniform photoluminescence and an elegant and silky feel in combination and can fully satisfy artistry as desired.

11 Claims, 3 Drawing Sheets

[FIG. 1]
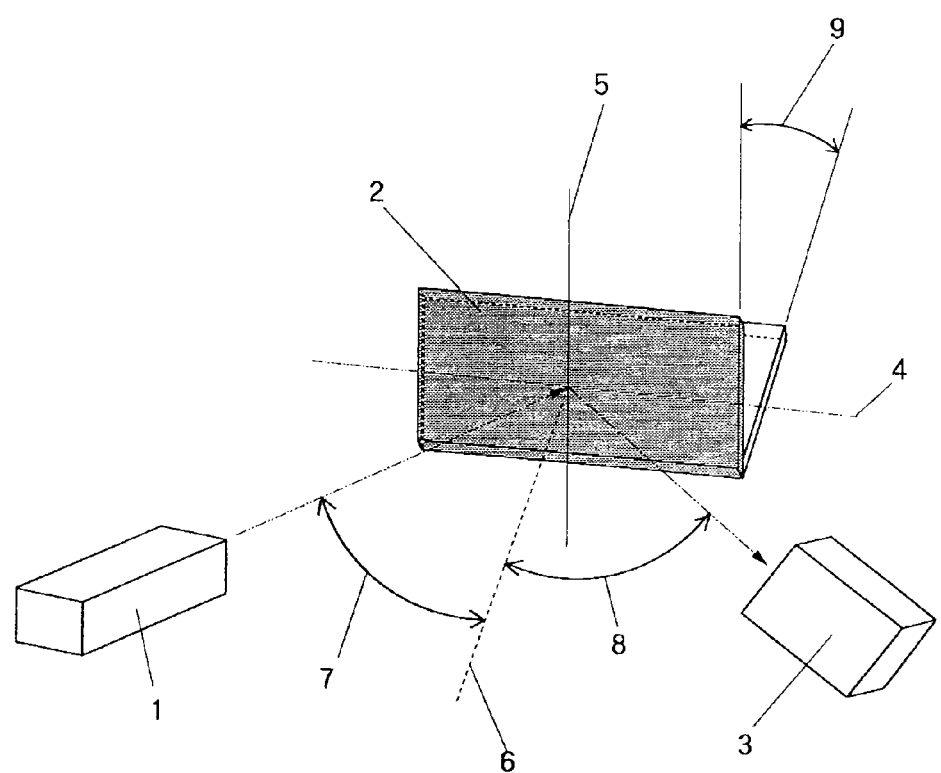

[FIG. 2]
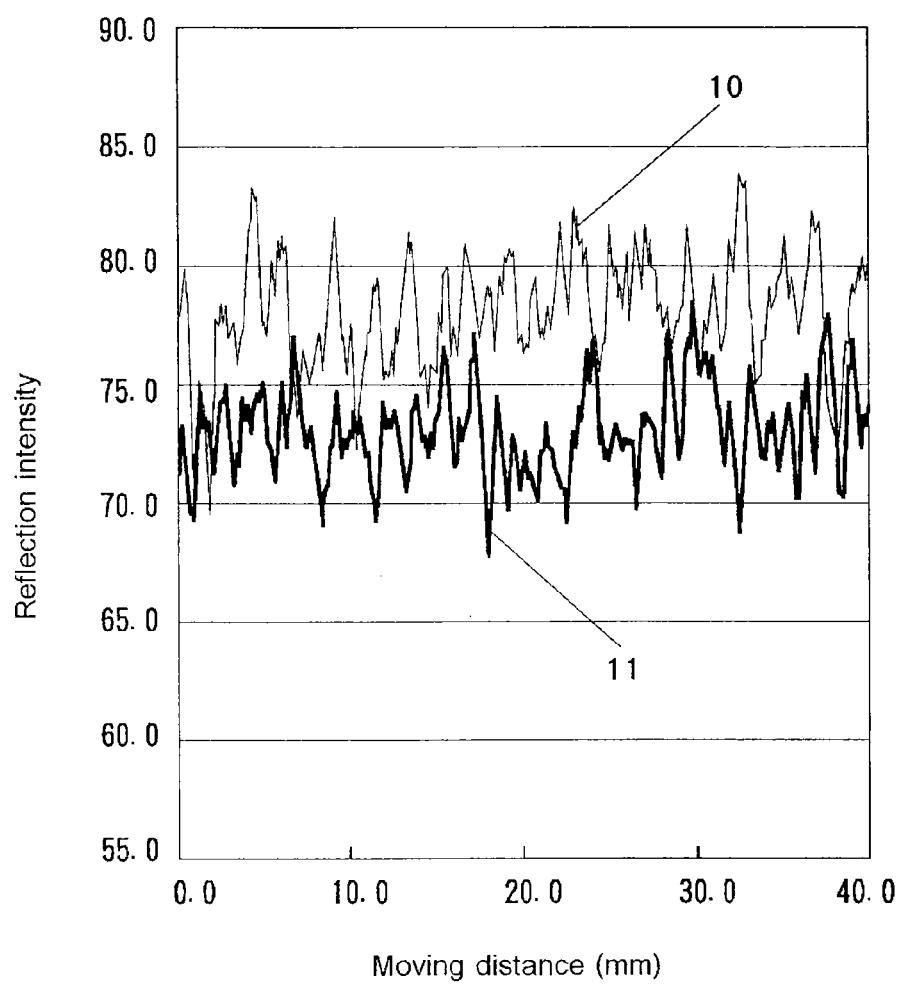

[FIG. 3]
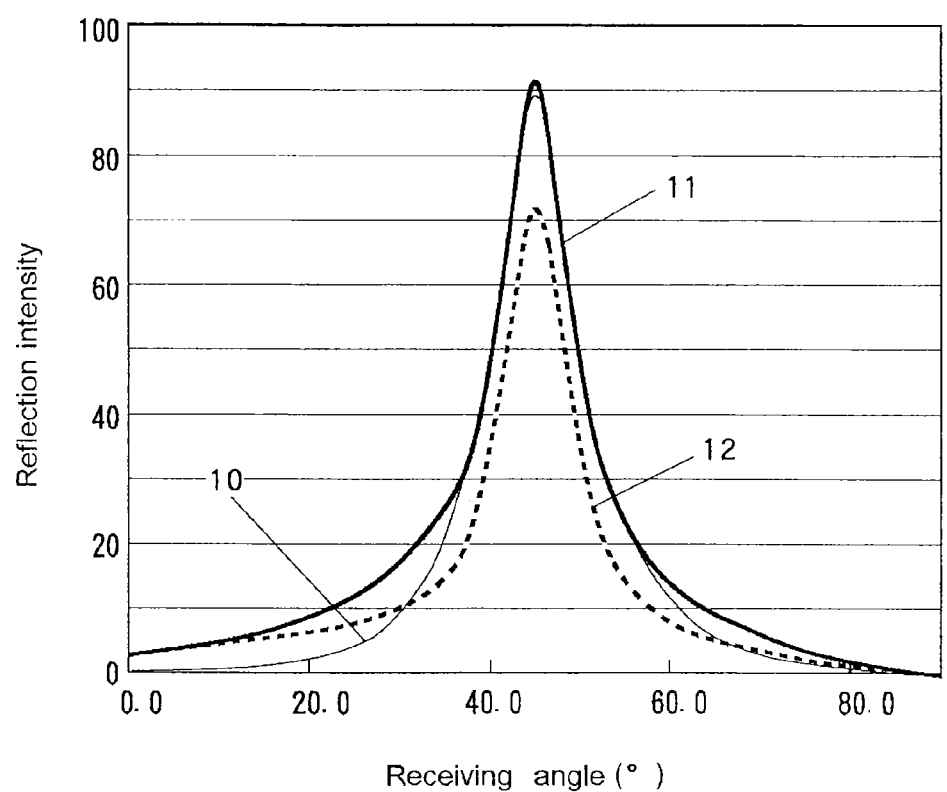

PEARLESCENT PIGMENT, PROCESS FOR PRODUCING THE SAME, COATING COMPOSITION AND MULTILAYERED COAT

This application is a divisional of U.S. patent application Ser. No. 11/992,977, filed Apr. 2, 2008, which is the U.S. National Phase of International Application No. PCT/JP2006/319713 filed on Oct. 2, 2006, and priority is claimed to Japan App. Ser. No. 2005-290148 filed Oct. 3, 2005. The contents of said applications, namely, U.S. patent application Ser. No. 11/992,977, International Application No. PCT/JP2006/319713, and Japan App. Ser. No. 2005-290148, are hereby incorporated by reference, in their entirety, into this application. This invention relates to a pearlescent pigment obtained by coating surfaces of specific flaky substrate particles (which may herein after be called simply "substrate particles") with a metal oxide, its production process, and its use.

TECHNICAL FIELD

Background Art

Known pearlescent pigments include those obtained by coating surfaces of substrate particles, such as mica flakes, with a metal oxide of large refractive index like titanium dioxide. In recent years, pearlescent pigments making use of thin alumina flakes as substrate particles improved in smoothness, heat resistance and transparency, in which mica flakes are deficient as substrate particles, have been proposed (Patent Document 1). However, when plate alumina produced by a hydrothermal process is used as substrate particles in the process described in the above patent document, adsorbability of particles of a metal oxide on the alumina is very low, and hence, the particles of the metal oxide are bound into large aggregates, thereby failing to provide a pigment equipped with satisfactory photoluminescence. Even if the metal oxide particles are adsorbed on the plate alumina, the particles of the metal oxide which cover the substrate particles are so large that wholly uniform photoluminescence, from which no graininess is felt, or smooth and elegant photoluminescence, that is, silky pearlescence is hardly available. It has, therefore, been unable to fully satisfy artistry required for various applications.
Patent Document 1: JP-A-09-255891

DISCLOSURE OF THE INVENTION

Problem to be Solved by the Invention

When the metal oxide coating is conducted using ordinary substrate particles, the pearlescence of the conventional pearlescent pigments is not uniform and is deficient in smoothness as a whole due to the inclusion of large substrate particles having a large average particle size and wide reflection areas as mentioned above, although it has discontinuous strong photoluminescence. In an attempt to overcome this problem, substrate particles of small average particle size were used. The above-described grainy feel was reduced, but it was still unable to derive any pearlescence having a smooth, elegant, photoluminescent and silky feel.

With the foregoing circumstances of the conventional art in view, therefore, an object of the present invention is, to provide a pearlescent pigment, which has, as a whole, both uniform photoluminescence and an elegant and silky feel and can fully satisfy artistry as required.

An other object of the present invention is to provide a coating composition capable of forming a coat having characteristic photoluminescence in a single-apply coating process, a 2-coat 1-bake coating process, a 3-coat 2-bake coating process or a coating process that forms at least one pearlescent coat layer between stacked at least one desired coat layers or on a coat layer.

Means for Solving the Problem

The above-described objects can be achieved by the present invention to be described herein after.

Described specifically, the present invention provides a pearlescent pigment comprising flaky alumina ("alumina flake") substrate particles produced by a hydrothermal process and coat layers formed on the substrate particles and composed of at least one metal oxide comprising at least a titanium oxide, wherein the metal oxide has an average particle size of from 1 to 500 nm.

In the above-described pearlescent pigment according to the present invention, it can be preferred that the coat layers of the metal oxide are mixed layers and/or stacked layers of two or more metal oxides comprising at least the titanium oxide; that the flaky alumina substrate particles have an average particle size of from 0.1 to 50 μm; that the alumina substrate particles have an aspect ratio (particle size/thickness) of from 5 to 500; that the alumina substrate particles have an average particle size a statistical variation coefficient of which is from 20 to 90; and that the pearlescent pigment has an average particle size a statistical variation coefficient of which is from 20 to 90.

The present invention also provides a process for the production of a pearlescent pigment, which comprises: dispersing in water flaky alumina substrate particles that have been produced by a hydrothermal process and whose surfaces have been activated, preferably by at least one method selected from a plasma treatment, a ultrasonic treatment, an acid treatment, an alkali treatment, a shock treatment or a chemical etching treatment; hydrolyzing in the resulting dispersion, a metal salt comprising at least a salt of titanium; allowing the resulting metal hydroxide or metal oxide to deposit on the surfaces of the alumina substrate particles; and then subjecting the resulting deposit to a heat treatment and forming, on the surfaces of the substrate particles, a metal oxide coat layer having a average particle size in a range from 1 to 500 nm.

Further, the present invention also provides a coating composition comprising the above-described pearlescent pigment of the present invention and a film-forming resin. Preferably, the coating composition can further contain a liquid medium.

Still further, the present invention also provides a multilayered coat comprising a base coat layer formed from the above-described coating composition of the present invention and a clear coat layer formed on the base coat layer.

Preferably, the above-described multilayered coat can have reflected light intensities having a statistical variation coefficient of not greater than 5 when measured by a photometer; or a 45°/0° reflection intensity ratio of not greater than 100 when measured at an elevation angle of not smaller than 0° by a goniophotometer.

Moreover, the present invention provides a multilayered coat comprising a colored first base coat layer formed on a surface of a substrate, a second base coat layer formed from the above-described coating composition of the present invention on the colored first base coat layer, and a clear coat layer formed on the second base coat layer; a multilayered coat comprising a first coat layer formed on a surface of a substrate and at least one second coat layer formed from the above-described coating composition of the present invention on the first coat layer; and also a multilayered coat comprising at least two first coat layers formed one over the other on a surface of a substrate and at least one second coat layer formed from a coating composition according to claim 8 between the at least two first coat layers.

Advantageous Effects of the Present Invention

The present inventors have proceeded with extensive research to achieve the above-described objects of the present invention. As a result, it has been found that color visions of a pearlescent pigment, which was obtained by activating surfaces of substrate particles obtained by a hydrothermal process and then by coating the substrate particles with at least one metal oxide of a particle size in a range of from 1 to 500 nm, and colored articles making use of the pigment have such artistry as giving a graininess-free, smooth, elegant, photoluminescent and silky color tone. In addition, it has also been found that, when the above-described various coats are formed on substrates by using coating compositions containing the above-described pearlescent pigment, the coats fully show good artistry.

BEST MODES FOR CARRYING OUT THE INVENTION

The present invention will next be described in further detail based on certain preferred embodiments.

The term "hydrothermal process" as used herein means a process that allows crystals of a substrate material such as alumina to grow in a solvent of high temperature and high pressure. Conditions for the crystal growth are specific to the chemical structure of the substrate material, the solvent, temperature and pressure used, and the like. It is, therefore, possible to synthesize desired substrate particles in accordance with an average particle size, an aspect ratio and the like, which are required for the substrate particles. The chemical and physical properties of the substrate particles produced by the hydrothermal process are unique properties not available from any process other than the hydrothermal process.

Substrate particles which can be obtained by the hydrothermal process can include alumina, boehmite, iron oxide, hydroxyapatite, zirconia, titanates, titanium oxide, cobalt hydroxide oxide, calcium silicate and the like. Any substrate particles may be used insofar as they have uniformity, smoothness, heat resistance, transparency and the like and provide artistry as required. However, preferred is alumina which satisfies the above-described conditions with a good balance. Flaky alumina substrate particles which are preferred as mentioned above are known by themselves, and are available for use in the present invention, for example, from Kinsei Matec Co., Ltd., for example, under the trade names of "YFA-02050" (average particle size: 2.0 µm, aspect ratio: 50), "YFA-07070" (average particle size: 7.0 µm, aspect ratio: 70), "YFA-05070" (average particle size: 5.0 µm, aspect ratio: 70), "YFA-10030" (average particle size: 10.0 µm, aspect ratio: 27), etc.

The average particle size of the substrate particles may be from 0.1 to 50 µm, preferably from 0.3 to 30 µm, more preferably from 0.5 to 20 µm. An average particle size greater than 50 µm is not preferred in that the resulting pearlescent pigment strongly reflects light to impair a silky color tone. On the other hand, an average particle size smaller than 0.1 µm is not preferred in that the resulting pearlescent pigment strongly scatters light to impair a silky color tone. The aspect ratio of the substrate particles may be from 5 to 500, preferably from 7 to 300, more preferably from 10 to 200. An aspect ratio smaller than 5 is not preferred in that the substrate particles is poor in orientation and interference light (pearlescence) is hardly available from the resulting pearlescent pigment. On the other hand, an aspect ratio greater than 500 is not preferred in that the substrate particles are prone to breakage during handling such as circulation, mixing and dispersion.

Further, the particle size distribution of the substrate particles may be from 20 to 90, preferably from 25 to 80, more preferably from 30 to 70 in terms of statistical variation coefficient (CV value). This CV value means the percentage of a standard deviation based on an average particle size in a particle size distribution, and indicates the degree of scattering of the particle size distribution. It is to be noted that each particle size distribution was measured by COULTER COUNTER MULTISIZER 3 (trade name; manufacture by Beckman Coulter, Inc.) and its statistical variation coefficient was also calculated.

When the CV value of the substrate particles is 20 or greater, small particle-size particles, which produce scattered light, and particles, which produce rather strong reflected light, are well-balanced so that the resulting pearlescent pigment can be provided with a silky color tone. When the CV value of the substrate particles is smaller than 20, on the other hand, the particle size distribution of the substrate particles is extremely narrow, but small particle-size particles, which produce scattered light, and large particle-size particles, which produce rather strong reflected light, both decrease, resulting in the lack of a balance between scattered light and reflected light so that the resulting pearlescent pigment is deprived of a silky color tone. On the other hand, a CV value of the substrate particles, which is greater than 90, is not preferred in that scattered light and reflected light are poorly balanced and the resulting pearlescent pigment is also provided with an impaired silky color tone.

The pearlescent pigment according to the present invention can be obtained by activating the surfaces of the substrate particles and then coating the surfaces with at least one metal oxide. In the pearlescent pigment according to the present invention, the metal oxide is required to have a particle size of from 1 to 500 nm, preferably from 3 to 300 nm, more preferably from 5 to 200 nm. When the particles size of the metal oxide with which the substrate particles are coated fall within the range of from 1 to 500 nm, the metal oxide has high crystallinity so that the refractive index inherent to the metal oxide is fully exhibited. Moreover, the top surfaces of the coats of the pearlescent pigment are smooth and produce sufficient reflected light. As a result, a satisfactory interference color is produced, so that graininess-free, smooth and elegant photoluminescence, that is, a silky feel is higher, thereby making it possible to fully satisfy artistry as desired.

It is to be noted that the above-described particle size indicates the particle size of metal oxide particles or aggregates of metal oxide particles after hydrolysis or sintering. The average particle size of each metal oxide was calculated from 50 particles chosen at random from a micrograph obtained by a scanning electron microscope, "FE-SEMS-4800" (tradename; manufactured by Hitachi, Ltd.)

When the particle size of the metal oxide exceed 500 nm, the metal oxide layers have substantial surface roughness so that reflected light from the pearlescent pigment is considerably weakened and no sufficient interference color is produced. When the particle size of the metal oxide is smaller than 1 nm, on the other hand, the metal oxide is provided with substantially reduced crystallinity so that the refractive index inherent to the metal oxide is not available. As a result, the pearlescent pigment does not produce any sufficient interference color. Even if the coats of the metal oxide are specified in thickness, a sufficient interference color cannot be obtained unless the metal oxide forming the coat layers is controlled in particle size.

By the coats of the metal oxide, the resulting pearlescent pigment is provided with a silver tone color or, when the coats is increased in thickness, with an interference color. Further, the surfaces of the substrate particles may be coated with a colored metal oxide, for example, with an iron oxide to obtain a reddish or blackish, pearlescent pigment. Furthermore, the pearlescent pigment may be provided with still higher saturation by adsorbing fine particles of a coloring pigment, which will be described subsequently herein, on the surfaces of the pearlescent pigment.

The pearlescent pigment according to the present invention can also be obtained by coating the surfaces of the above-described substrate particles with a mixture of two or more metal oxides or by stacking and coating two or more metal oxide layers stepwise on the surfaces of the above-described substrate particles. By coating with such a mixture or by conducting such stacking and coating, physical properties not available from a single metal oxide alone can be obtained, for example, light resistance, water resistance and the like can be improved. Especially by successively stacking two or more metal oxides into an increased number of layers, a pearlescent pigment of still higher photoluminescence can be obtained.

Furthermore, the pearlescent pigment according to the present invention may preferably have a particle size distribution the statistical variation coefficient (CV value) ranges from 20 to 90. Its reasons are similar to those mentioned above in connection with the substrate particles.

A description will next be made of the process of the present invention for the production of the pearlescent pigment. The pearlescent pigment can be obtained by coating the surfaces of the substrate particles with the metal oxide having the particle size of from 1 to 500 nm.

For a general pearlescent pigment, it is necessary to control the particle size of a metal oxide to be deposited on substrate particles after hydrolysis or sintering and the aggregation property of the particles such that the particles of the metal oxide are arrayed on the surfaces of the substrate surfaces. The process described in Patent Document 1 referred to in the above, however, is practically impossible to control the particle size, aggregation and arraying of the metal oxide, and therefore, cannot obtain a pearlescent pigment capable of producing sufficient interference light, because substrate particles produced by a hydrothermal process are extremely high in surface smoothness and have low adsorbing ability for the metal oxide on their surfaces, and the aggregation of the metal oxide itself tends to proceed easily. As a result, the metal oxide exists as large aggregates and has low adsorbability on the surfaces of the substrate particles. Even when adsorbed, the resulting coats of the metal oxide are not uniform in thickness and the top surfaces of the coats become rough. Accordingly, reflected light is considerably weakened so that no sufficient interference color is produced.

Even if the substrate particles produced by the hydrothermal process are coated with the metal oxide by a known technique and moreover, the resulting coats are specified in thickness, it is still impossible to control the particle size and aggregation property of the metal oxide forming the coat layers and to obtain a pearlescent pigment having a sufficient interference color unless the adsorbing ability of the surfaces of the substrate particles is improved.

In the present invention, it was found that by activating beforehand the surfaces of the substrate particles produced by the hydrothermal process, the particles of the metal oxide can be evenly adsorbed as fine particles on the surfaces of the substrate particles. For the above-described surface activation, usable examples include plasma treatments such as thermal plasma treatment and low-temperature plasma treatment, ultrasonic treatment, acid treatment, alkali treatment, tumbling-medium-assisted dispersion treatment, shock treatments such as high-pressure shock treatment and sand blasting treatment, ozone treatment, and chemical etching treatments such as electrochemical treatment. These treatments can be applied either singly or in combination.

Treatment gas usable in plasma treatment can be one of or a combination of two or more of nitrogen, ammonia, a mixed nitrogen-hydrogen gas, oxygen-containing gases such as oxygen, ozone, water vapor, carbon monoxide, carbon dioxide, nitrogen monoxide and nitrogen dioxide, rare gases such as helium, argon, neon and xenon, halogen gases such as fluorine, chlorine and iodine, and mixed gases obtained by mixing fluorocarbon gases, such as tetra fluorocarbon, hexa fluorocarbon and hexa fluoropropylene, in oxygen-containing gases at volume ratios not greater than ½.

Examples of a method for generating the above-described plasma include the method that a direct current is applied to a gas to effect plasma decomposition, the method that a radiofrequency voltage is applied to a gas to effect plasma decomposition, the method that a gas is subjected to plasma decomposition by electron cyclotron resonance, and the method that a gas is thermally decomposed by a hot filament.

As the pressure of the treatment gas upon the above-described plasma treatment, $1 \times 10^{-4}$ to 100 Torr is preferred because a low pressure requires a costly vacuum chamber and vacuum pumping system. The actual treatment gas pressure is appropriately determined depending on the excitation means within the above-described pressure range. However, $1 \times 10^{-2}$ to 100 Torr is more preferred because it is possible to apply a direct current or radiofrequency current capable of generating a plasma even when the system is simple and the treatment gas pressure is relatively high.

The inputted electric power required for the above-described plasma treatment differs depending on the area and shape of electrodes. Lower electric power results in a low plasma density so that more time is required for the treatment. On the other hand, higher electric power induces uneven treatment. The electric power may, therefore, be from 20 to 200 W preferably.

When the construction of the electrodes employed in the above-described plasma treatment is the parallel plate type, the coaxial cylinder type, the curved counter plate type or the hyperbolic counter plate type, a voltage is applied by the capacity coupling method. When a radiofrequency voltage is applied, it can be applied in an induction manner by using external electrodes. The distance between the electrodes is appropriately determined depending on the treatment pressure and the substrate particles, and can be set desirably at a possible shortest distance for plasma treatment because a longer distance leads to a lower plasma density and requires higher electric power.

The time of the plasma treatment is determined depending on the inputted electric power. In general, however, 1 to 60 minutes are preferred because a shorter plasma treatment time cannot achieve a sufficient degree of activation of the substrate particles while no significant improvement can be expected in the degree of activation of the substrate particles even when the plasma treatment time is made excessively long. Concerning the temperature during the plasma treatment, neither heating nor cooling is absolutely needed.

The above-described plasma treatment is required to be evenly applied over the entire surfaces of the flaky substrate particles. It is, therefore, preferred to conduct the plasma treatment while rolling the flaky substrate particles. Such mixing methods can include the method that the flaky substrate particles are sealed in a vessel and are tumbled together with the vessel and the method that the flaky substrate particles are mixed by vibrations. An appropriate mixing method can be determined depending on the particle size and amount of the flaky substrate particles to be treated.

Any ultrasonic oscillator can be used in the ultrasonic treatment insofar as its oscillating frequency is in a range of from 50 Hz to 100 KHz and its output power is in a range of from 20 to 1,000 W. An oscillating frequency lower than 50 Hz leads to a substantial reduction in the surface uniformity of the energy distribution of ultrasonic waves striking the flaky substrate particles, and hence to insufficient activation. An oscillating frequency higher than 100 KHz, on the other hand, leads to a substantial reduction in the overall energy density, and also to insufficient activation of the substrate particles. Even within the above-described range, cavitations may still occur depending on the structure and material of a tank to be used and on the kind of a dispersing medium to be used. In such a case, it is desired to increase the oscillation frequency or to lower the output power such that the treatment system can be kept under conditions which do not cause cavitations.

In the present invention, ultrasonic vibrations can be applied either continuously or intermittently. It is, however, preferred to apply ultrasonic vibrations by controlling them to appropriate conditions within the above-described frequency range of from 50 Hz to 100 KHz and the above-described power output range of from 20 to 1,000 W.

An acid usable in the acid treatment can be one of or a combination of two or more of inorganic acids such as hydrochloric acid, nitric acid, sulfuric acid, phosphoric acid and carbonic acid, organic acids such as acetic acid, citric acid and benzoic acid, and resin acids such as acrylic resins and rosin. An alkali usable in the alkali treatment can be one of or a combination of two or more of alkali metal salts such as caustic soda and caustic potash, alkaline earth metal salts such as calcium hydroxide, and weak bases such as ammonia, sodium carbonate, aniline and phenol.

The concentration and temperature of an acid or alkali solution in the acid treatment or alkali treatment may be in a range of from 0.1 to 99 wt % and a range of from 5 to 95 C.°, respectively, although an efficient treatment temperature may be more preferably from 15 to 70° C. The treatment time is suitably determined depending on the concentration and temperature, with a range of from 5 minutes to 6 hours being preferred. The acid or alkali treatment may be repeated twice or more, or the acid and alkali treatments may be alternately conducted at least once. The acid treatment or alkali treatment also effects a pH adjustment, so that a pH buffer may be used. Further, a surfactant, organic solvent and/or the like may also be used as aid(s) in combination.

The shock treatment is a method for physically activating the substrate particles. Specific methods include partial grinding of the surfaces of the substrate particles by shaking or collision, and also, polishing by tumbling. Treatment methods which can achieve such partial grinding or polishing include dispersing shock treatment by a homogenizer, dissolver, sand mill, high-speed mixer or paint conditioner, high-pressure shock treatment by a high-pressure homogenizer, sand blasting treatment, jet mill treatment, and the like.

The concentration of the substrate particles in the liquid medium in the shock treatment may be from 1 to 200 wt %, with from 5 to 150 wt % being preferred. A concentration lower than 1 wt % results in a poor shock efficiency, while a concentration higher than 200 wt % results in thickening so that the shock treatment is rendered difficult. For the shock treatment that needs a medium upon effecting the same, glass beads, steel balls, zirconia beads and the like can be used, and the weight ratio of the medium to the substrate particles may be from 0 to 1,000 wt %, preferably from 0 to 500 wt %. It is not particularly needed to use a medium when the activation of the surfaces of the substrate particles can be sufficiently achieved by the collision of the substrate particles themselves.

In the shock treatment, a pH buffer may be used. Further, a surfactant, organic solvent and/or the like may also be used as aid(s) in combination. The time of the shock treatment is determined depending on the concentration of the substrate particles and the type and amount of the medium. However, the substrate particles cannot be provided with a sufficient degree of activation when the time of the shock treatment becomes short, and no substantial improvement can be expected in the activation degree of the substrate particles even when the time of the shock treatment is made excessively long. Therefore, 1 to 60 minutes are preferred in general. It is to be noted that the above-described physical activation treatment requires the payment of an attention to substantial changes in particle size distribution and CV value because, when the intensity of shock on the substrate particles is increased, the treatment is not limited to the surface activation of the substrate particles and may also break the substrate particles.

In addition, other conventional treatments, including chemical etching treatments such as ozone treatment, UV treatment and electrochemical treatment, can also be used widely.

The pearlescent pigment according to the present invention can also be obtained by adsorbing a hydrated oxide of a metal such as titanium, zirconium, tin or iron with a particle size of from 1 to 500 nm on the surface-treated substrate particles by a known method, for example, by a method that thermally hydrolyzes a salt of the metal in water in which the substrate particles have been dispersed or by a method that subjects the salt of the metal to neutralization hydrolysis with an alkali in the water; and then by calcining the hydrated oxide. By conducting this calcination step in a reducing atmosphere, the metal oxide is converted into a low-valence titanium oxide or a low-valence iron oxide, so that a pearlescent pigment tinged in a black color can be obtained. Additional artistry can be also imparted by a known method in addition to the use of the metal oxide.

The atomic weight of the metal in the water-soluble metal salt required to obtain pearlescence (interference color) may be from $2.0 \times 10^{-5}$ mol to $2.0 \times 10^{-1}$ mol, more preferably from $4.0 \times 10^{-5}$ mol to $1.0 \times 10^{-1}$ mol. If the atomic weight of the metal is lower than $2.0 \times 10^{-5}$ mol, the flaky substrate particles cannot be coated so that no interference light is produced. If the atomic weight of the metal exceeds $1.0 \times 10^{-1}$ mol, inconveniences arise in that, even if the flaky substrate particles can be coated, cracks tend to occur in the coat layers after calcinations, and as a result, the intensity of interference light is lowered.

A description will next be made about the coating composition according to the present invention. The coating composition according to the present invention contains the above-described pearlescent pigment of the present invention and a film-forming resin, and preferably, may contain the pearlescent pigment and film-forming resin in a liquid medium. Usable examples of the film-forming resin include, but are not limited to, film-forming resins employed in the field of conventionally-known coating compositions, such as acrylic resins, acrylic melamine resins, vinyl chloride-vinyl acetate copolymer resins, alkyd resins, polyester resins, polyurethane resins and amino resins.

As a solvent for dissolving or dispersing the pearlescent pigment and film-forming resin, one conventionally and commonly known to be useful in coating compositions can be used. Specific examples include water, toluene, xylene, butyl acetate, methyl acetate, acetone, methyl ethyl ketone, methyl isobutyl ketone, methanol, ethanol, butanol, cyclohexane, and the like. These solvents may also be used as mixed solvents.

In the coating composition according to the present invention, the pearlescent pigment of the present invention may be used in a proportion of from 0.005 to 50 parts by weight, preferably from 0.1 to 30 parts by weight per 100 parts by weight of the film-forming resin. Use of the pearlescent pigment in a proportion of smaller than 0.005 parts by weight cannot obtain a coating composition the provision of which is one of the objects of the present invention. On the other hand, use of the pearlescent pigment in a proportion of greater than 50 parts by weight can obtain a coating composition the provision of which is one of the objects of the present invention, but is not preferred because the resulting coats are provided with reduced physical properties.

In the present invention, the above-described pearlescent pigment can be used singly or in combination with one or more other pigments. As coloring pigments usable in combination, pigments employed in ordinary coating compositions and the like can be used. Specific examples include phthalocyanine pigments, quinacridone pigments, perylene pigments, anthraquinone pigments, DPP pigments, metal complex pigments, transparent iron oxide pigments, carbon black, titanium oxide, and zinc oxide. Further, as metal powder pigments, aluminum powder, copper powder, stainless steel powder, and the like can be mentioned. Among these, aluminum powder is used most commonly. As special metal pigments, metal colloids and the like can be used. As mica pigments usable in combination in the present invention, conventionally-known mica pigments can be widely used in combination, and illustrative are transparent pearl mica and colored mica. As light interference pigments, interference mica, interference alumina, interference mica (interference glass) and the like can be mentioned. In addition, one or more of fillers, antistatic agents, stabilizers, antioxidants, UV absorbers and the like can also be added as needed in the coating composition according to the present invention.

When the coating composition according to the present invention contains the pearlescent pigment of the present invention and another pigment, a base coating composition containing the pearlescent pigment of the present invention and another base coating composition containing the another pigment can be prepared beforehand and these two types of base coating compositions can then be blended together into the coating composition as desired, or as an alternative, the pearlescent pigment and the another pigment can be mixed together at the beginning and can then be formulated into the coating composition.

The coating composition obtained as described above is applied onto a substrate such as a metal plate, glass plate, ceramic plate or plastic plate, to which surface preparation may have been applied as needed, by spray coating, electrostatic coating, flow coating, roll coating or the like, dried and then crosslinked and cured to form a colored coat layer.

The coat formed by applying the coating composition of the present invention onto a substrate has a color tone of a graininess-free, smooth, elegant and silky feel, compared with conventional $TiO_2$-based pearlescent pigments for coatings. Owing to the possession of the above-described properties, coats having excellent characteristic photoluminescence, which are not seen on coats available from conventional coating compositions, can be formed in a single-apply coating process, a 2-coat 1-bake coating process, a 3-coat 2-bake coating process or a coating process that forms, with a coating composition containing the pearlescent pigment of the present invention, at least one coat layer between stacked at least one desired coat layers or on a coat layer.

A coat can also be formed by using the above-described colored coat layer as a base coat layer; applying a clear coating composition, which has been prepared by dissolving or dispersing a resin having low compatibility with the above-described film-forming resin in an organic solvent, on the base coat layer; drying the clear coating composition; and then subjecting it to heat treatment. The coat formed by applying the coating composition of the present invention onto the substrate has graininess-free, smooth, elegant, silky photoluminescence. Namely, the pearlescent pigment according to the present invention is formed of uniform particles, and therefore, is free of a localized strong photoluminescent feel associated with large particles and has continuous uniform photoluminescence. Moreover, reflected light and scattered light are well-balanced, thereby presenting a smooth, elegant and silky feel.

A localized strong photoluminescent feel occurs as a result of discontinuous specular reflection of light, which has entered into the coat, by the pearlescent pigment. A difference between a localized strong photoluminescent feel and a uniform photoluminescent feel can be quantitated by measuring specular light intensities of a continuous surface of a coat, statistically calculating the degrees of scattering, that is, the dissemination of the specular light intensities, and comparing their variances with each other. No particular limitation is imposed on a photometer insofar as it can measure the specular light intensities of the continuous surface of the coat, but preferred is a photometer which can measure specular light intensities while moving a surface of a specimen in the direction of an X-axis on the system. As a specific example, a three-dimensional goniophotometer, "GP-200" (trade name; manufactured by Murakami Color Research Laboratory Co., Ltd.), or the like can satisfy the above-mentioned measurement conditions.

A coat obtained from the coating composition according to the present invention is provided with uniform, graininess-free, smooth photoluminescence in visual perception when its quantitated variance is 5 or smaller. When its quantitated variance is greater than 5, on the other hand, the coat is provided with glaring, grainy photoluminescence in visual perception and cannot be provided with uniform, graininess-free, smooth photoluminescence in visual perception.

Light, which has entered into a coat, is separated into specular light and scattered light, and is reflected out of the coat. By balancing the specular light and the scattered light with each other, a smooth, elegant, silky color tone is obtained as visual perception. Light other than specular light scatters in all directions, and exists as three-dimensional scattered light. By three-dimensionally capturing the specular light and the three-dimensional scattered light, a perception close to a state that they are viewed by the human can be reproduced. The above-mentioned specular light can be measured by a photometer shown in the system. No particular limitation is imposed on the photometer insofar as it can measure the reflection intensity at a desired elevation angle while changing the receiving angle. Preferred is, however, a three-dimensional goniophotometer which can continuously measure reflected light. As a specific example, a three-dimensional goniophotometer, "GP-200", or the like can satisfy the above-mentioned measurement conditions.

A silky feel of a coat can be quantitated by measuring the intensities of reflected light and scattered light at a desired elevation angle with a three-dimensional goniophotometer; measuring the reflection intensity at 45° receiving angle, which is in the neighborhood of specular light, and the reflection intensity at 0° receiving angle, which corresponds to representative scattered angle; and then determining the intensity ratio (45°/0°) of the intensity at 45° to that at 0°. A coat obtained from the coating composition according to the present invention is provided with a smooth, elegant, silky photoluminescent feel in visual perception when the (45°/0°) reflection intensity ratio of the intensity at 45° receiving angle to that at 0° receiving angle is 100 or smaller. When the (45°/0°) reflection intensity ratio of the intensity at 45 receiving angle to that at 0° receiving angle is greater than 100, on the other hand, no silky photoluminescent feel can be obtained in visual perception.

The pearlescent pigment according to the present invention has a small particle size and a large aspect ratio so that, even when its content is high in a coat, it is oriented and the surface smoothness is not lost. Because the pearlescent pigment according to the present invention is a pearlescent pigment making use of chemically-uniform plate particles produced by a hydrothermal process, it is also unique in optical characteristics, is excellent in the balance between reflected light and scattered light, presents photoluminescence of a graininess-free, smooth, elegant and silky feel, and can provide a coat of excellent finish. In a coated color making use of a general pearlescent pigment, on the other hand, the adoption of a small average particle size results in non-uniform plate particles having a small aspect ratio and the fine pigment is not oriented in the resulting coat, leading to a drawback that the coat is provided with significantly-reduced photoluminescence or the smoothness of a clear finish is impaired. As an optical characteristic, reflected light and scattered light are poorly balanced so that an elegant and silky feel cannot be obtained.

The pearlescent pigment according to the present invention is extremely good, as it is, as a pigment for ceramics, plastics, inks, toners, inkjet inks and cosmetics. Further, depending on these applications, treatments are applied the pearlescent pigment to impart water resistance, weatherability, chemical resistance, color fastness and high dispersibility as needed, and the thus-treated pearlescent pigment is used for the respective applications.

EXAMPLES

The present invention will next be described in further detail based on Examples and Comparative Examples, although the present invention shall not be limited by the following Examples. It is to be noted that in the following Examples and Comparative Examples, the designations of "parts" and "%" are on a weight basis.

Production Examples of Pearlescent Pigments

Example 1

"YFA-02050" (average particle size: 2.0 µm, aspect ratio: 50, CV value: 45), plate alumina produced by a, hydrothermal process (hydrothermally produced alumina), (20 g) was placed in a flask having an internal capacity of 1 L. After the interior of the flask was depressurized to 0.05 Torr, a radiofrequency voltage of 13.56 MHz was applied under an oxygen atmosphere at 0.11 Torr by a powder plasma treatment system ("PT-500", tradename; manufactured by Samco International, Inc.) to conduct plasma treatment at room temperature for 5 minutes (inputted electric power: 40 W).

In another flask having an internal capacity of 1 L, sodium sulfate (anhydride, 20 g) was added to desalted water (300 mL) and was dissolved with stirring. To the resultant solution, the plate alumina (20 g) which had been subjected to plasma treatment as described above was added, followed by dispersion with stirring. A solution (28 g) of titanium chloride, the titanium concentration of which was 16.5%, was charged into the dispersion. The thus-obtained mixture was stirred and heated for 4 hours under reflux. Subsequently, insoluble solid matter was collected by filtration, washed with water, dried, and then subjected to heat treatment at 700° C. for 1 hour. Water was added to the thus-obtained treated matter, and with stirring, the free salts were caused to dissolve. Insoluble solid matter was then collected by filtration, washed with water and dried to obtain $TiO_2$-coated plate alumina (Example 1).

Example 2

"YFA-07070" (average particle size: 7.0 µm, aspect ratio: 70, CV value: 44), hydrothermally produced alumina, (20 g) was placed in a flask having an internal capacity of 1 L, and desalted water (300 mL) was added to disperse the alumina with stirring. The dispersion was subjected to ultrasonic treatment (inputted electric power: 180 W, frequency: 20 KHz) at room temperature for 15 minutes by an ultrasonic processor ("UD-200", trade name; manufactured by Tomy Seiko Co., Ltd.). Subsequently, sodium sulfate (anhydride, 20 g) was added and was dissolved with stirring. A solution (20 g) of titanium chloride, the titanium concentration of which was 16.5%, was charged into the dispersion. The thus-obtained mixture was stirred and heated for 4 hours under reflux. Insoluble solid matter was then collected by filtration, washed with water, dried, and then subjected to heat treatment at 700° C. for 1 hour. Water was added to the thus-obtained treated matter, and with stirring, the free salts were caused to dissolve. Insoluble solid matter was then collected by filtration, washed with water and dried to obtain $TiO_2$-coated plate alumina (Example 2).

Example 3

"YFA-05070" (average particle size: 5.0 µm, aspect ratio: 70, CV value: 37), hydrothermally produced alumina, (20 g) was placed in a flask having an internal capacity of 1 L, and desalted water (300 mL) was added to disperse the alumina with stirring. 35% hydrochloric acid (20 g) was charged into the dispersion, followed by acid treatment at room temperature for 15 minutes.

Sodium sulfate (anhydride, 40 g) was then added and dissolved with stirring. A 16.5% solution (30 g) of titanium chloride and a 50% solution (1.9 g) of stannic chloride were charged into the dispersion. The thus-obtained mixture was stirred and heated for 4 hours under reflux. Further, insoluble solid matter was collected by filtration, washed with water, dried, and then subjected to heat treatment at 800° C. for 30 minutes. Water was added to the thus-obtained treated matter, and with stirring, the free salts were caused to dissolve. Insoluble solid matter was then collected by filtration, washed with water and dried to obtain mixed $TiO_2$/$SnO_2$-coated plate alumina (Example 3).

Example 4

"YFA-02050", hydrothermally produced alumina, (20 g) was placed in a flask having an internal capacity of 1 L, and desalted water (300 mL) was added to disperse the alumina with stirring. Caustic soda (10 g) was added to the dispersion, followed by alkali treatment at room temperature for 15 minutes. Using 35% hydrochloric acid, the pH of the mixture was then adjusted to pH 2, and sodium sulfate (anhydride, 40 g) was added and then dissolved with stirring. A solution (28 g) of titanium chloride, the titanium concentration of which was 16.5%, and a 50% solution (1.0 g) of stannic chloride were charged into the dispersion. The thus-obtained mixture was stirred and heated for 4 hours under reflux.

Insoluble solid matter was then collected by filtration, washed with water, dried, and then subjected to heat treatment at 800° C. for 30 minutes. Water was added to the thus-obtained treated matter, and with stirring, the free salts were caused to dissolve. Insoluble solid matter was then collected by filtration, washed with water and dried to obtain mixed $TiO_2$/$SnO_2$-coated plate alumina (Example 4).

Example 5

"YFA-07070", hydrothermally produced alumina, (20 g) was placed in a flask having an internal capacity of 1 L, and desalted water (300 mL) was added to disperse the alumina with stirring. The dispersion was subjected to ultrasonic treatment (inputted electric power: 180 W, frequency: 20 KHz) at room temperature for 15 minutes by the ultrasonic processor ("UD-200"). Nitric acid (20 g) was then charged, followed by acid treatment at room temperature for 15 minutes.

A 50% solution (1.0 g) of stannic chloride was charged into the dispersion, and the resulting mixture was adjusted to pH 6.0 with a solution of sodium hydroxide. Subsequently, insoluble solid matter was collected by filtration, washed with water, and then dried to obtain $SnO_2$-coated plate alumina. Sodium sulfate (anhydride, 20 g) was dissolved in desalted water (300 mL). In the thus-obtained solution, the above-described $SnO_2$-coated plate alumina which had been crushed was added and dispersed. A solution (20 g) of titanium chloride, the titanium concentration of which was 16.5%, was charged into the dispersion. The thus-obtained mixture was stirred and heated for 4 hours under reflux. Subsequently, insoluble solid matter was collected by filtration, washed with water, dried, and then subjected to heat treatment at 800° C. for 1 hour. Water was added to the thus-obtained treated matter, and with stirring, the free salts were caused to dissolve. Insoluble solid matter was then collected by filtration, washed with water and dried to obtain stacked $SnO_2$/$TiO_2$-coated plate alumina (Example 5).

Example 6

"YFA-07070", hydrothermally produced alumina, (20 g) was placed in a plastic bottle having an internal capacity of 250 mL, and desalted water (100 mL) and 2-mm glass beads (100 g) were added, followed by shock treatment for 30 minutes on a paint conditioner. Desalted water (200 mL) was then added to the dispersion, and the resultant mixture was stirred. A 50% solution (1.0 g) of stannic chloride was charged into the dispersion, and the resulting mixture was adjusted to pH 6.0 with a solution of sodium hydroxide. Subsequently, insoluble solid matter was collected by filtration, washed with water, and then dried to obtain $SnO_2$-coated plate alumina.

Sodium sulfate (anhydride, 20 g) was dissolved in desalted water (300 mL). In the thus-obtained solution, the above-described $SnO_2$-coated plate alumina which had been crushed was added and dispersed. A solution (20 g) of titanium chloride, the titanium concentration of which was 16.5%, was charged into the dispersion. The thus-obtained mixture was stirred and heated for 4 hours under reflux. Subsequently, insoluble solid matter was collected by filtration, washed with water, dried, and then subjected to heat treatment at 800° C. for 1 hour. Water was added to the thus-obtained treated matter, and with stirring, the free salts were caused to dissolve. Insoluble solid matter was then collected by filtration, washed with water and dried to obtain stacked $SnO_2$/$TiO_2$-coated plate alumina (Example 6).

Example 7 & Example 8

"YFA-10030" (average particle size: 10.0 µm, aspect ratio: 27, CV value: 50), hydrothermally produced alumina, (20 g) was placed in a flask having an internal capacity of 1 L. After the interior of the flask was depressurized to 0.05 Torr, a radiofrequency voltage of 13.56 MHz was applied under a water vapor atmosphere at 0.11 Torr by the powder plasma treatment system ("PT-500") to conduct plasma treatment at room temperature for 5 minutes (inputted electric power: 40 W). In another flask having an internal capacity of 1 L, sodium sulfate (anhydride, 20 g) was added to desalted water (300 mL) and was dissolved with stirring. To the resultant solution, the plate alumina (20 g) which had been subjected to plasma treatment as described above was added, followed by dispersion with stirring.

On the side, a solution (50 g) of titanium chloride, the titanium concentration of which was 16.5%, was dissolved in desalted water (300 mL) to provide a solution A. After the plate alumina dispersion was adjusted to pH 2.0 with hydrochloric acid and was heated to 80° C., the solution A was charged at a constant rate over 4 hours by a metering pump until the substrate particles were provided with an interference silver color. During the charging, a 10% solution of sodium hydroxide was added to maintain the pH of the dispersion at 2.0 and the temperature of the dispersion was also maintained at 80° C.

After the solution A was charged until the substrate particles were provided with the interference silver color, the dispersion was heated for 1 hour under reflux.

Subsequently, insoluble solid matter was collected by filtration, washed with water, dried, and then subjected to heat treatment at 700° C. for 1 hour. Water was added to the thus-obtained treated matter, and with stirring, the free salts were caused to dissolve. Insoluble solid matter was then collected by filtration, washed with water and dried to obtain TiO$_2$-coated plate alumina (Example 7). Further, TiO$_2$-coated plate alumina (Example 8) was obtained by conducting similar processing as in Example 7 except that the hydrothermally-produced alumina was changed to "YFA-07070".

Comparative Example 1

Sodium sulfate (anhydride, 20 g) was added to desalted water (300 mL) and was dissolved with stirring. To the resultant solution, plate alumina A (average particle size: 55 µm, aspect ratio: 30, CV value: 95)(20 g) which was not a hydrothermal product was added, followed by dispersion with stirring. A solution (30 g) of titanium chloride, the titanium concentration of which was 16.5%, was charged into the dispersion. The thus-obtained mixture was stirred and heated for 4 hours under reflux. Subsequently, insoluble solid matter was collected by filtration, washed with water, dried, and then subjected to heat treatment at 700° C. for 1 hour. Water was added to the thus-obtained treated matter, and with stirring, the free salts were caused to dissolve. Insoluble solid matter was then collected by filtration, washed with water and dried to obtain TiO$_2$-coated plate alumina (Comparative Example 1).

Comparative Example 2

Sodium sulfate (anhydride, 20 g) was added to desalted water (300 mL) and was dissolved with stirring. To the resultant solution, plate alumina B (average particle size: 10 µm, aspect ratio: 4.0, CV value: 60)(20 g) which was not a hydrothermal product was added, followed by dispersion with stirring. A solution (30 g) of titanium chloride, the titanium concentration of which was 16.5%, was charged into the dispersion. The thus-obtained mixture was stirred and heated for 4 hours under reflux. Subsequently, insoluble solid matter was collected by filtration, washed with water, dried, and then subjected to heat treatment at 700° C. for 1 hour. Water was added to the thus-obtained treated matter, and with stirring, the free salts were caused to dissolve. Insoluble solid matter was then collected by filtration, washed with water and dried to obtain TiO$_2$-coated plate alumina (Comparative Example 2).

Comparative Example 3

TiO$_2$-coated plate alumina (Comparative Example 3) was obtained as in Example 1 except that the plate alumina ("YFA-02050") was used without the plasma treatment.

Comparative Example 4

TiO$_2$-coated plate alumina (Comparative Example 4) was obtained as in Example 2 except that the plate alumina ("YFA-07070") was used without the ultrasonic treatment.

Comparative Example 5

Mixed TiO$_2$/SnO$_2$-coated plate alumina (Comparative Example 5) was obtained as in Example 3 except that the plate alumina ("YFA-05070") was used without the acid treatment.

Comparative Example 6

Mixed TiO$_2$/SnO$_2$-coated plate alumina (Comparative Example 6) was obtained as in Example 4 except that the plate alumina ("YFA-02050") was used without the alkali treatment.

Comparative Example 7

A commercial product composed of mica coated with titanium oxide, "IRIODIN 225 WII" (trade name, product of Merck Ltd., Japan), was provided as Comparative Example 7.

The average particle sizes (µm), aspect ratios and CV values of the substrate particles used in Examples 1-8 and Comparative Examples 1-6 and the particle sizes (nm) and CV values of the metal oxides of the pearlescent pigments obtained in Examples 1-8 and Comparative Examples 1-7 were determined and presented together in Table 1. Each average particle size and its corresponding aspect ratio were calculated from 50 particles chosen at random from a micrograph obtained by a scanning electron microscope "ERA-8000" (manufactured by Elionix Inc.). Each CV value is a value calculated as a statistical variation coefficient based on a measurement performed by using "COULTER COUNTER MULTISIZER 3". The average particle size of each metal oxide was calculated from 50 particles chosen at random from a micrograph obtained by "FE-SEM S-4800".

TABLE 1

|  | Flaky alumina substrate particles | | | | Pearlescent pigment | |
| --- | --- | --- | --- | --- | --- | --- |
|  | Kind | Average particle size (µm) | Aspect ratio | CV value | Particle size of metal oxide (nm) | CV value |
| Example 1 | "YFA-02050" | 2.0 | 50 | 45 | 45 | 47 |
| Example 2 | "YFA-07070" | 7.0 | 70 | 44 | 40 | 47 |
| Example 3 | "YFA-05070" | 5.0 | 70 | 37 | 80 | 40 |
| Example 4 | "YFA-02050" | 2.0 | 50 | 45 | 75 | 47 |
| Example 5 | "YFA-07070" | 7.0 | 70 | 44 | 40 | 45 |
| Example 6 | "YFA-07070" | 7.0 | 70 | 44 | 40 | 47 |
| Example 7 | "YEA-10030" | 10.0 | 27 | 50 | 50 | 53 |
| Example 8 | "YFA-07070" | 7.0 | 70 | 44 | 50 | 45 |
| Comp. Ex. 1 | Plate alumina A | 55 | 30 | 95 | 45 | 97 |
| Comp. Ex. 2 | Plate alumina B | 10 | 4.0 | 60 | 45 | 65 |
| Comp. Ex. 3 | "YFA-02050" | 2.0 | 50 | 45 | 920 | 70 |
| Comp. Ex. 4 | "YFA-07070" | 7.0 | 70 | 44 | 740 | 55 |
| Comp. Ex. 5 | "YFA-05070" | 5.0 | 70 | 37 | 870 | 62 |
| Comp. Ex. 6 | "YFA-02050" | 2.0 | 50 | 45 | 1,020 | 70 |
| Comp. Ex. 7 | — | — | — | — | 300 | 50 |

Production Example of Automotive Paints

This example illustrates production and evaluation examples upon using the pearlescent pigments of the present invention as coating compositions. Evaluated formulation examples are presented together in Table 2.

TABLE 2

(Unit: parts)

| Formulation No. | Pearlescent pigment | | Acrylic varnish (solid content: 60%) | Melamine varnish (solid content: 60%) | "SOLVESSO #100" | Butyl acetate |
|---|---|---|---|---|---|---|
| Formulation A | Example 1 | 30 | 82 | 34 | 21 | 9 |
| Formulation B | Example 2 | 30 | 82 | 34 | 21 | 9 |
| Formulation C | Example 3 | 30 | 82 | 34 | 21 | 9 |
| Formulation D | Example 4 | 30 | 82 | 34 | 21 | 9 |
| Formulation E | Example 5 | 30 | 82 | 34 | 21 | 9 |
| Formulation F | Example 6 | 30 | 82 | 34 | 21 | 9 |
| Formulation G | Example 7 | 30 | 82 | 34 | 21 | 9 |
| Formulation H | Example 8 | 30 | 82 | 34 | 21 | 9 |
| Formulation I | Comp. Ex. 1 | 30 | 82 | 34 | 21 | 9 |
| Formulation J | Comp. Ex. 2 | 30 | 82 | 34 | 21 | 9 |
| Formulation K | Comp. Ex. 3 | 30 | 82 | 34 | 21 | 9 |
| Formulation K | Comp. Ex. 4 | 30 | 82 | 34 | 21 | 9 |
| Formulation M | Comp. Ex. 5 | 30 | 82 | 34 | 21 | 9 |
| Formulation N | Comp. Ex. 6 | 30 | 82 | 34 | 21 | 9 |
| Formulation O | Comp. Ex. 7 | 30 | 82 | 34 | 21 | 9 |
| Formulation P | None | 0 | 82 | 34 | 21 | 9 |

Mixtures of the formulations A-H were separately subjected to simple dispersion processing in a sand mill. Further, the resulting dispersion (50 parts, each) of the formulations A-H and a mixture (50 parts) of the formulation P were combined into intimate mixtures, respectively, to obtain coating compositions A-H (Table 3). Those coating compositions each contained 8.55 parts of the pearlescent pigment per 100 parts of the coating composition, and will be referred to as "example paint A-H".

Mixtures of the formulations I-O were separately subjected to simple dispersion processing in a sand mill. Further, the resulting dispersion (50 parts, each) of the formulations I-O and a mixture (50 parts) of the formulation P were combined into intimate mixtures, respectively, to obtain coating compositions I-O (Table 3). Those coating compositions each contained 8.55 parts of the pearlescent pigment per 100 parts of the coating composition, and will be referred to as "comparative example paint I-O".

The example paints A-H, which contained the pearlescent pigments obtained above in Examples 1-8, respectively, and the comparative example paints I-O, which contained the pearlescent pigments obtained above in Comparative Examples 1-7, respectively, were applied on black coat paper sheets by a bar coater (No. 6), respectively. After dried at room temperature for 30 minutes, the paints were baked and cured at 120° C. for 30 minutes to prepare coated specimens.

With respect to each of those coated specimens, the uniformity of photoluminescence was evaluated visually and was also measured by a three-dimensional goniophotometer ("GP-200") under the following conditions: reflectance measurement, light source: A light, incident angle: 45°, receiving angle: 45°, receiver slit: 0.4 mm square, moving measurement over 40 mm along X-axis on specimen surface, data sampling intervals: 0.1 mm; and the statistic variance of the reflection intensity was calculated. The measuring instrument is depicted in FIG. 1, one example of graphs obtained by the measurements is shown in FIG. 2, and the measurement results are presented in Table 3.

Further, graininess-free, smooth conditions of each coated specimen were evaluated visually and were also measured by the three-dimensional goniophotometer ("GP-200") under the following conditions: reflectance measurement, light source: A light, incident angle: 45°, receiving angles: 45° and 0°, elevation angle: 2.5°; and the reflection intensity ratio (45°/0°) was calculated. One example of graphs obtained by the measurements is shown in FIG. 3, and the measurement results are presented in Table 3.

TABLE 3

| | Coating composition | Uniformity of photoluminescence | | Silky feel | |
|---|---|---|---|---|---|
| | | Variance | Visual evaluation | Reflection intensity ratio (45°/0°) | Visual evaluation |
| Example 1 | Example paint A | 4.2 | A | 25.1 | A |
| Example 2 | Example paint B | 4.3 | A | 40.6 | A |
| Example 3 | Example paint C | 3.6 | A | 33.6 | A |
| Example 4 | Example paint D | 3.2 | A | 30.4 | A |
| Example 5 | Example paint E | 4.9 | A | 66.7 | A |
| Example 6 | Example paint F | 3.5 | A | 48.8 | A |
| Example 7 | Example paint G | 4.3 | A | 71.2 | A |
| Example 8 | Example paint H | 3.6 | A | 57.9 | A |
| Comp. Ex. 1 | Comp. Ex. paint I | 5.9 | B | 210 | B |
| Comp. Ex. 2 | Comp. Ex. paint J | 6.2 | B | 141 | B |
| Comp. Ex. 3 | Comp. Ex. paint K | 7.1 | B | 220 | B |
| Comp. Ex. 4 | Comp. Ex. paint L | 6.2 | B | 130 | B |
| Comp. Ex. 5 | Comp. Ex. paint M | 6.5 | B | 180 | B |
| Comp. Ex. 6 | Comp. Ex. paint N | 6.8 | B | 215 | B |
| Comp. Ex. 7 | Comp. Ex. paint O | 5.9 | B | 210 | B |

A: good,
B: poor

Compared with the comparative example paints, the example paints were lower in variance that indicates the degree of scattering of photoluminescence and had uniform photoluminescence as a whole. In addition, the example paints were lower in reflection intensity ratio at receiving angles 45° and 0° than the comparative example paints, and also had a smooth and silky feel well-balanced in specular light and scattered light.

Moreover, cosmetics, plastics, ceramics, inks, toners and inkjet ink compositions which contain pearlescent pigments of the present invention also have, as a whole, both uniform photo luminescence and graininess-free, smooth and elegant photoluminescence, that is, a silky feel, and can fully satisfy artistry as required.

INDUSTRIAL APPLICABILITY

The pearlescent pigment according to the present invention has, as a whole, uniform photoluminescence and a color tone having a graininess-free, smooth and elegant photoluminescence, that is, a silky feel, and therefore, is optimal for fields where such a color tone is required, for example, for fields such as ceramics, resins, paints, construction materials, inks, toners, inkjet ink compositions and cosmetics and also for fields where artistry is required.

BRIEF DESCRIPTION OF THE DRAWINGS

FIG. 1 A schematic depicting a measuring instrument.
FIG. 2 A measurement graph of variations in reflection intensity against the moving distance along an X-axis.
FIG. 3 A measurement graph of variations in three-dimensional gonioreflectance (elevation angle: 2.5°).
1: Light source
2: Specimen
3: Photoreceptor
4: X-axis
5: Y-axis
6: Z-axis
7: Incident angle
8: Receiving angle
9: Elevation angle
10: Comparative example paint O
11: Comparative example paint C
12: Comparative example paint A

The invention claimed is:

1. A process for producing a pearlescent pigment, comprising steps of:
    forming a dispersion by (1) treating surfaces of substrate particles consisting of alumina flakes produced by a hydrothermal process and then dispersing in a solution comprising water the surface-treated alumina flake substrate particles, or by (2) dispersing the substrate particles consisting of alumina flakes produced by a hydrothermal process in a solution comprising water and then treating surfaces of the dispersed alumina flake substrate particles in the solution;
    adding at least one metal salt to the dispersion comprising the water and the alumina flake substrate particle whose surface has been treated in the treating step,
    hydrolyzing in the resulting dispersion the at least one metal salt so as to form metal hydroxide or metal oxide;
    allowing the resulting metal hydroxide or the resulting metal oxide obtained from the hydrolyzing step to deposit on said surface of said alumina flake substrate particle having been treated, in the dispersion; and then
    subjecting the resulting deposit to a heat treatment so as to form, on said surface of said alumina flake substrate particle, a metal oxide coat layer of at least one metal oxide derived from the at least one metal salt, in the pearlescent pigment,
    wherein the at least one metal oxide in the metal oxide coat layer consists of (i) titanium oxide or (ii) a combination of titanium oxide and one additional metal oxide material selected from the group consisting of zirconium oxide, tin oxide, iron oxides, and mixtures thereof,
    wherein the metal oxide coat layer is formed directly on the surface of the alumina flake substrate particle,
    wherein the at least one metal oxide or an aggregate of the at least one metal oxide in the metal oxide coat layer has an average particle size in a range from 1 to 500 nm,
    wherein the treating of the surface of the alumina flake substrate particles has been conducted prior to the adding step, by an acid treatment, where an acid used for the acid treatment comprises at least one resin acid,
    wherein the surface treating step improves adsorption of particles of the at least one metal oxide to the surface of the alumina flake substrate particle, and
    wherein the produced pearlescent pigment provides a coat having an intensity ratio 45°/0° in a range of 100 or smaller, when the coat is formed of a coating composition including the pearlescent pigment, where the intensity ratio 45°/0° is a ratio of a reflection intensity at 45° as a receiving angle relative to a refection intensity at 0° as a receiving angle.

2. The process according to claim 1, wherein the acid used for the acid treatment comprises the at least one resin acid in combination with at least one inorganic acid, or with at least one organic acid, or with at least one inorganic acid and at least one organic acid,
    wherein the at least one inorganic acid is selected from the group consisting of hydrochloric acid, nitric acid, sulfuric acid, phosphoric acid, and carbonic acid, and
    the at least one organic acid is selected from the group consisting of acetic acid, citric acid, and benzoic acid.

3. The process according to claim 1, wherein a statistical variation coefficient of an average particle size of said alumina flake substrate particles is from 20 to 90.

4. The process according to claim 1, wherein a statistical variation coefficient of an average particle size of the resulting pearlescent pigment is from 20 to 90.

5. The process according to claim 1, wherein said at least one metal oxide in the metal oxide coat layer is the combination of the titanium oxide and the one additional metal oxide material.

6. The process according to claim 1, wherein the process further comprises a step of stacking one or more additional metal oxide layers on the metal oxide coat layer formed on said alumina flake substrate particles.

7. The process according to claim 6, wherein said additional metal oxide layers are each obtained by coating with one or more metal oxides comprising at least titanium oxide.

8. The process according to claim 1, wherein an average particle size of the at least one metal oxide or an aggregate of the at least one metal oxide in the metal oxide coat layer is in a range from 3 to 300 nm.

9. The process according to claim 1, wherein the process produces pearlescent pigment that provides a coat formed of a coating composition including the pearlescent pigment and having specular light intensities with quantitated variance of 5 or smaller, when measured with a photometer.

10. The process according to claim 1, wherein the hydrolyzing the at least one metal salt in the resulting dispersion is performed under a heated-reflux condition.

11. The process according to claim 1, wherein the acid treatment is performed as the treating of the surfaces of the substrate particles in the forming step for a treatment time in a range from 5 minutes to 6 hours.

* * * * *